United States Patent
Isoda et al.

(10) Patent No.: US 10,959,787 B2
(45) Date of Patent: Mar. 30, 2021

(54) MEDICAL MANIPULATOR SYSTEM

(71) Applicant: OLYMPUS CORPORATION, Tokyo (JP)

(72) Inventors: Takumi Isoda, Tokyo (JP); Mitsuaki Hasegawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 309 days.

(21) Appl. No.: 16/032,153

(22) Filed: Jul. 11, 2018

(65) Prior Publication Data

US 2018/0325607 A1 Nov. 15, 2018

Related U.S. Application Data

(63) Continuation of application No. PCT/JP2016/050974, filed on Jan. 14, 2016.

(51) Int. Cl.
*A61B 34/00* (2016.01)
*A61B 1/00* (2006.01)
(Continued)

(52) U.S. Cl.
CPC .......... *A61B 34/25* (2016.02); *A61B 1/00009* (2013.01); *A61B 1/0016* (2013.01);
(Continued)

(58) Field of Classification Search
CPC ......... A61B 34/25; A61B 34/71; A61B 90/06; A61B 1/00009; A61B 1/00133; A61B 1/00135
See application file for complete search history.

(56) References Cited

U.S. PATENT DOCUMENTS 6,557,558 B1    5/2003   Tajima et al.
7,831,096 B2 *  11/2010  Williamson, Jr. ..... A61B 34/20
                                                         382/195
(Continued)

FOREIGN PATENT DOCUMENTS

EP    1080695 A1    3/2001
EP    2394799 A1   12/2011
(Continued)

OTHER PUBLICATIONS

International Search Report dated Mar. 15, 2016 issued in PCT/JP2016/050974.

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

A medical manipulator system having a controller configured to receive an image showing a state of a treating portion of a manipulator from an endoscope, determine a magnitude of an external force exerted on the manipulator based on the state of the treating portion of the manipulator shown in the image, generate an auxiliary image in which a display form thereof is changed with a change in the magnitude of the external force exerted on the manipulator determined, determine a display position of the auxiliary image in the image on the basis of the magnitude of the external force exerted on the manipulator determined, and generate a composited image signal of a composited image in which the auxiliary image is superimposed on the image on the basis of the display position determined.

8 Claims, 7 Drawing Sheets

(51) Int. Cl.
  *A61B 90/00*    (2016.01)
  *G06T 11/00*    (2006.01)
  *H04N 5/445*    (2011.01)
  *A61B 34/30*    (2016.01)
  *G06T 7/70*     (2017.01)

(52) U.S. Cl.
  CPC ...... *A61B 1/00133* (2013.01); *A61B 1/00135* (2013.01); *A61B 1/00149* (2013.01); *A61B 1/00154* (2013.01); *A61B 34/71* (2016.02); *A61B 90/06* (2016.02); *G06T 11/00* (2013.01); *H04N 5/44504* (2013.01); *A61B 2034/256* (2016.02); *A61B 2034/301* (2016.02); *A61B 2090/064* (2016.02); *A61B 2090/065* (2016.02); *A61B 2090/067* (2016.02); *A61B 2090/365* (2016.02); *G06T 7/70* (2017.01); *G06T 11/001* (2013.01); *G06T 2210/62* (2013.01)

(56) References Cited

U.S. PATENT DOCUMENTS

| | | | |
|---|---|---|---|
| 9,947,091 B2* | 4/2018 | Govari | A61B 6/032 |
| 2008/0004603 A1 | 1/2008 | Larkin et al. | |
| 2009/0192523 A1* | 7/2009 | Larkin | B25J 9/1671 |
| | | | 606/130 |
| 2009/0192524 A1 | 7/2009 | Itkowitz et al. | |
| 2009/0326553 A1 | 12/2009 | Mustufa et al. | |
| 2010/0331855 A1 | 12/2010 | Zhao et al. | |
| 2011/0015786 A1* | 1/2011 | Kawai | A61B 1/0016 |
| | | | 700/256 |
| 2013/0166070 A1* | 6/2013 | Zhao | B25J 9/1689 |
| | | | 700/259 |
| 2014/0055489 A1 | 2/2014 | Itkowitz et al. | |
| 2014/0058564 A1* | 2/2014 | Zhao | A61B 34/30 |
| | | | 700/259 |
| 2014/0135792 A1* | 5/2014 | Larkin | A61B 34/37 |
| | | | 606/130 |
| 2014/0195052 A1 | 7/2014 | Tsusaka et al. | |
| 2015/0073265 A1* | 3/2015 | Popovic | A61B 1/00045 |
| | | | 600/424 |
| 2015/0377613 A1* | 12/2015 | Small | G06T 15/08 |
| | | | 348/45 |
| 2017/0282372 A1* | 10/2017 | Itkowitz | A61B 34/30 |
| 2020/0078103 A1* | 3/2020 | Duindam | A61B 10/04 |
| 2020/0129239 A1* | 4/2020 | Bianchi | A61B 34/20 |

FOREIGN PATENT DOCUMENTS

| | | |
|---|---|---|
| JP | H07-184923 A | 7/1995 |
| JP | 2001-061860 A | 3/2001 |
| JP | 2001-104333 A | 4/2001 |
| JP | 2001-150368 A | 6/2001 |
| JP | 2007-029232 A | 2/2007 |
| JP | 2012-213655 A | 11/2012 |
| JP | 2014-097431 A | 5/2014 |
| JP | 2014-148037 A | 8/2014 |
| JP | 2015-163172 A | 9/2015 |
| WO | WO 2010/090059 A1 | 8/2010 |

* cited by examiner

MEDICAL MANIPULATOR SYSTEM

CROSS-REFERENCE TO RELATED APPLICATIONS

This is a continuation of International Application PCT/JP2016/050974 which is hereby incorporated by reference herein in its entirety.

TECHNICAL FIELD

The present invention relates to a medical manipulator system.

BACKGROUND ART

There is a known medical manipulator system with which an affected portion is treated by using a treatment tool that is attached to a manipulator inserted into the body while observing an image acquired by an endoscope inserted into the body (for example, see Patent Literature 1).

With the medical manipulator system of Patent Literature 1, an auxiliary image which is acquired by means of computation and in which a manipulator is composited in a semi-transparent manner is displayed by being superimposed on a real image acquired by an endoscope. The auxiliary image displays the position at which the manipulator should be disposed on the basis of an operation instruction given by a control portion.

CITATION LIST

Patent Literature

{PTL 1} U.S. Patent Application Publication No. 2014/135792

SUMMARY OF INVENTION

A first aspect of the present invention is a medical manipulator system including: a manipulator having a treating portion at a distal end thereof; an endoscope configured to capture an image showing a state of the treating portion performing treatment; an external-force detecting means for detecting data on an external force exerted on the manipulator; a display for an operator; and a controller comprising a hardware including at least one processor. The at least one processor is configured to: receive the data from the external-force detecting means; generate an auxiliary image in which a display form thereof is changed on the basis of the data; receive the image from the endoscope; determine a display position of the auxiliary image in the image on the basis of the data; generate a signal being capable to display a composited image which is superimposed on the auxiliary image on the image on the basis of the display position; and transmit the signal to the display.

A second aspect of the present invention is a controller of a medical manipulator system including a manipulator, an endoscope, and a display for an operator. The controller comprises at least one processor configured to: receive data on an external force exerted on the manipulator from an external-force detecting means being configured to generate the data; generate an auxiliary image in which a display form thereof is changed on the basis of the data; receive the image from the endoscope; determine a display position of the auxiliary image in the image on the basis of the data; generate a signal being capable to display a composited image which is superimposed on the auxiliary image on the image on the basis of the display position; and transmit the signal to the display.

A third aspect of the present invention is a method of controlling a medical manipulator system including a manipulator, an endoscope, and a display for an operator. The method includes: detecting an external force exerted on the manipulator; generating an auxiliary image in which a display form thereof is changed on the basis of the external force; receiving an image from the endoscope; determining a display position of the auxiliary image in the image on the basis of the external force; generating a signal being capable to display a composited image which is superimposed on the auxiliary image on the image on the basis of the display position; transmitting the signal to the display; and showing the composited image on the display.

DESCRIPTION OF EMBODIMENTS

A medical manipulator system 1 according to a first embodiment of the present invention will be described below with reference to the drawings.

Figure 1:
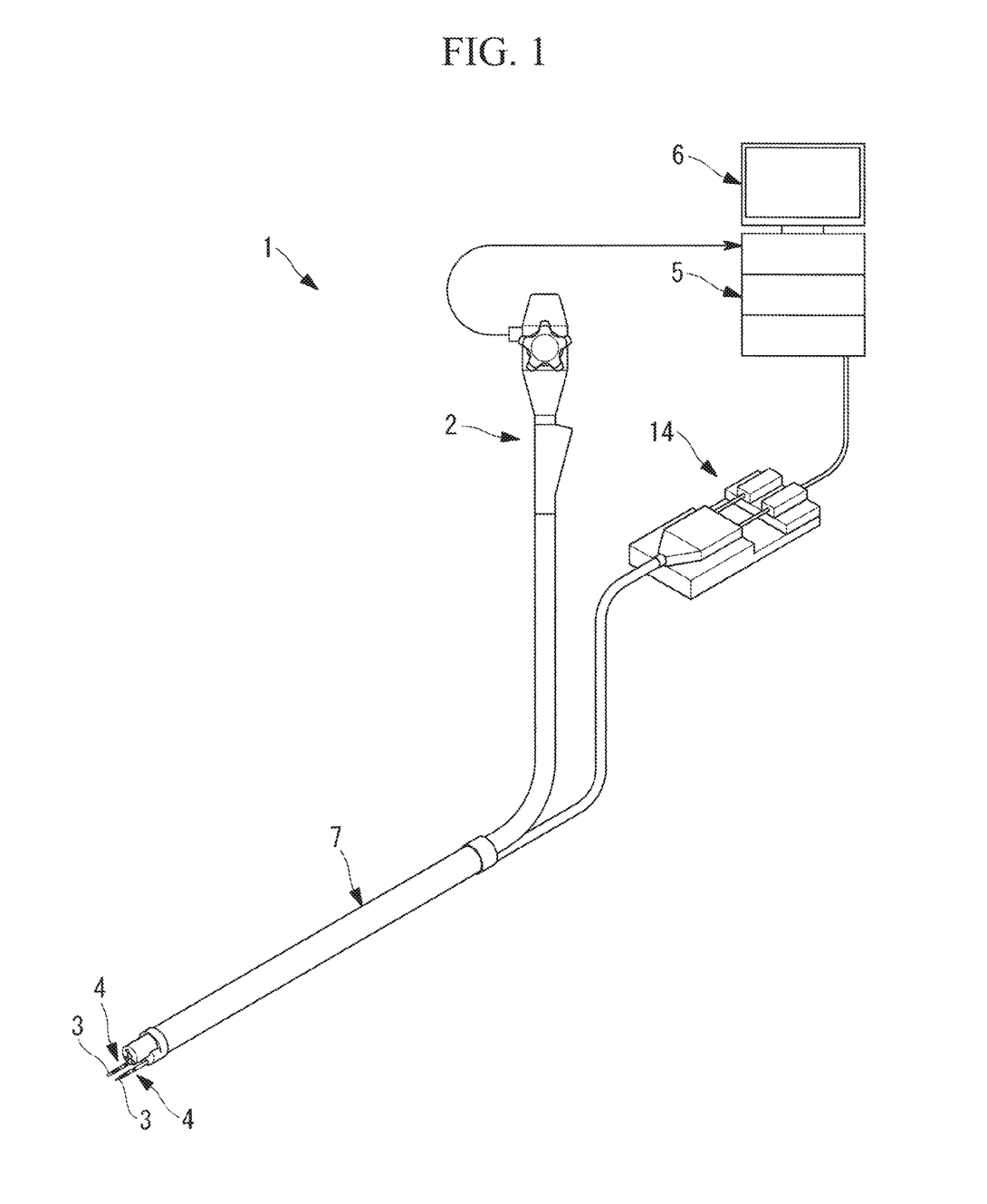
FIG. 1 is an overall configuration diagram showing a medical manipulator system according to a first embodiment of the present invention.

As shown in FIG. 1, the medical manipulator system 1 according to this embodiment is provided with: an endoscope 2, a manipulator 4 having a treating portion 3 at a distal end thereof; a control portion 5 that controls the manipulator 4; and a display portion 6.

Figure 2:
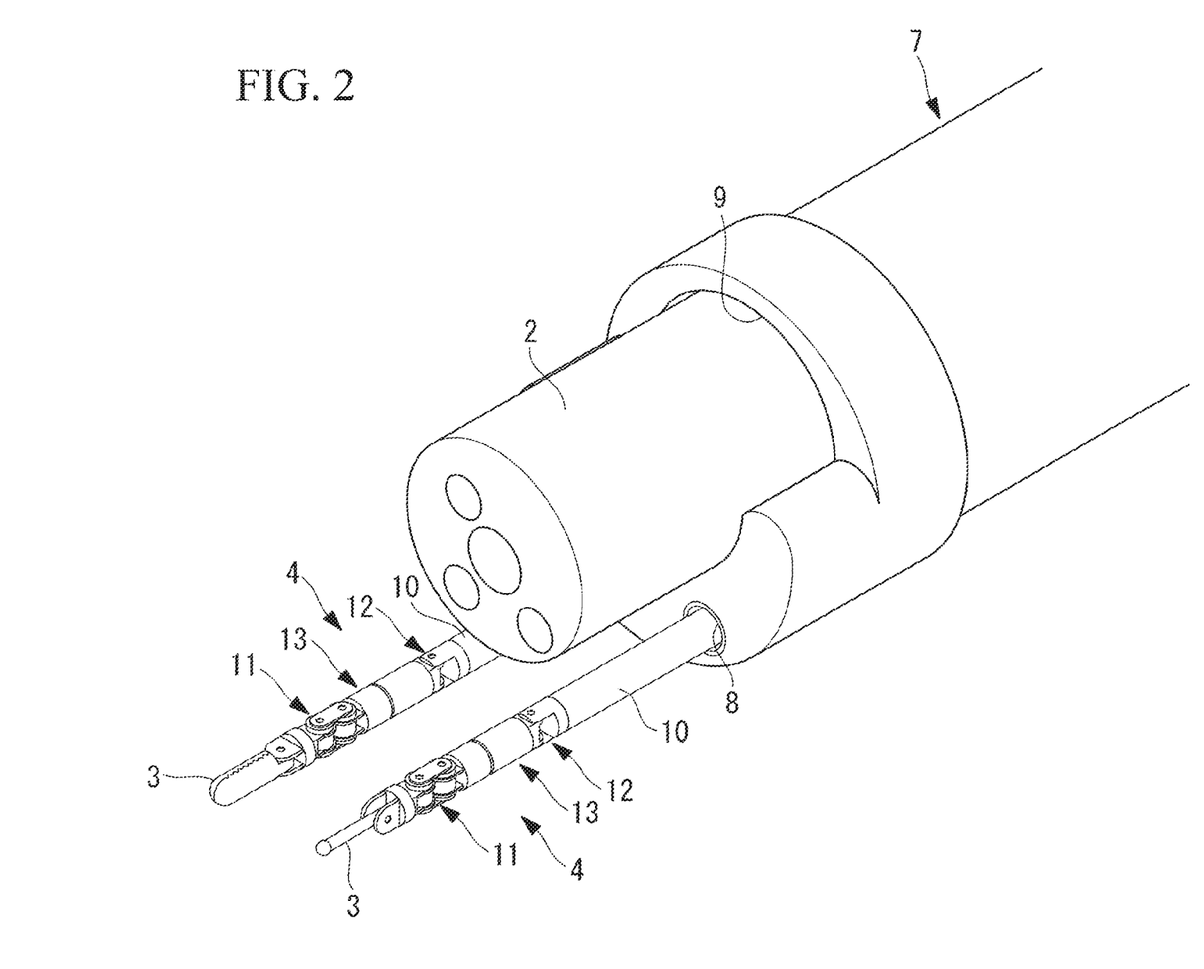
FIG. 2 is a perspective view showing a distal-end portion of an overtube of the medical manipulator system in FIG. 1.

The endoscope 2 and the manipulator 4 are individually inserted into lumens 8 and 9 of an overtube 7 that is inserted into the body of a patient. When the overtube 7 is inserted into the body so that a distal end thereof faces an affected portion X, as shown in FIG. 2, it is possible to acquire an image of the body interior including the affected portion X by using the endoscope 2, which is made to protrude from an opening of the lumen 9, which is provided at a distal end of the overtube 7, and it is possible to treat the affected portion X by using the treating portion 3 of the manipulator 4, which is similarly made to protrude from an opening of the lumen 8.

The manipulator 4 is provided with, for example: a flexible inserted portion 10 that is inserted into the lumen 8 of the overtube 7; a movable portion 13 that has one or more joints 11 and 12 provided at a distal end of the inserted portion 10; the treating portion 3 provided at a distal end of the movable portion 13; and a driving portion 14 that is provided at a proximal end of the inserted portion 10 and that drives the movable portion 13 by means of a wire (not shown).

Figure 3:
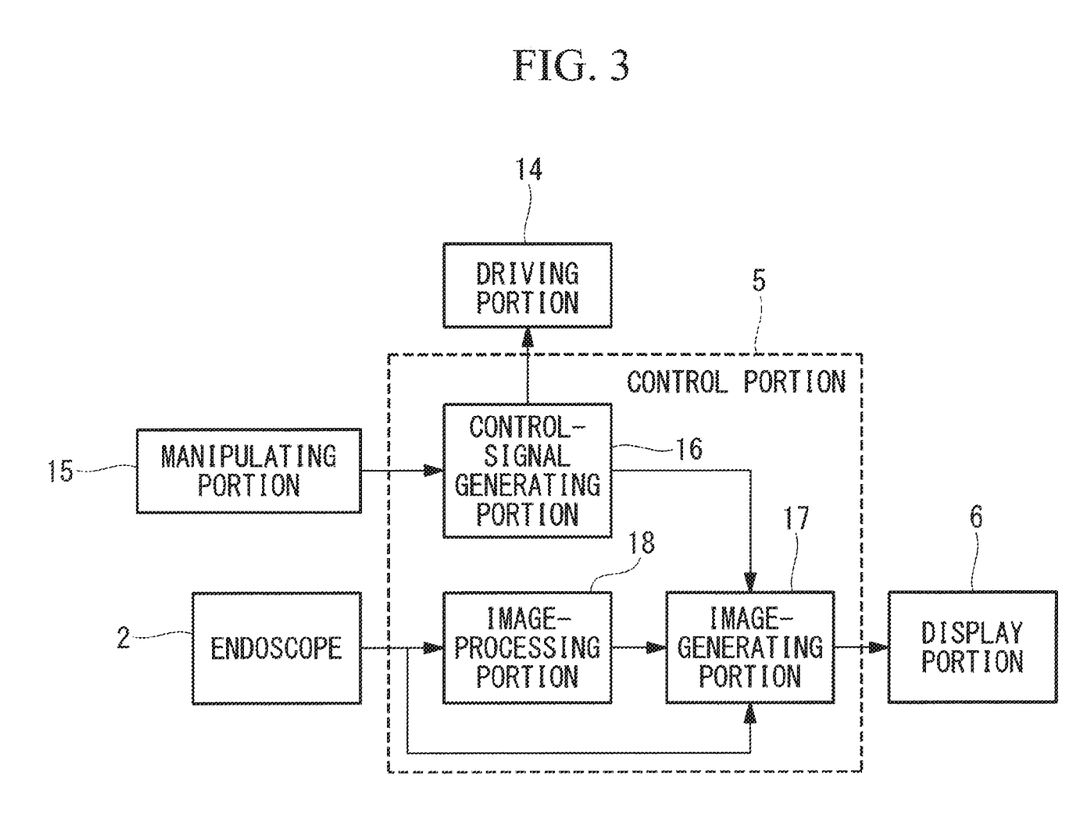
FIG. 3 is a block diagram for explaining a control portion of the medical manipulator system in FIG. 1.

As shown in FIG. 3, the control portion 5 is provided with: a control-signal generating portion (control portion) 16; an image-generating portion 17; and an image-processing portion (external-force detecting portion) 18. The control-signal generating portion 16 generates control signals for operating the driving portion 14 on the basis of manipulation inputs that are input via an operating portion 15 manipulated by an operator, The image-generating portion 17 generates a pseudo image (auxiliary image) of the manipulator 4 on the basis of the control signals generated by the control-signal generating portion 16, and generates a composited image in which the generated pseudo image is superimposed on the real image acquired by means of image capturing performed by the endoscope 2. The image-processing portion 18 detects an external force exerted on the manipulator 4 by processing the real image acquired by the endoscope 2.

The image-generating portion 17 calculates, on the basis of the control signals, positions of the individual joints 11 and 12 of the manipulator 4 by using a kinematics equation, and generates, by means of computer graphics, a pseudo image that represents the shapes of the treating portion 3 and manipulator 4 wherein the individual joints 11 and 12 are disposed at the calculated positions.

The image-processing portion 18 identifies, by applying image processing to the real image acquired by the endoscope 2, the positions of the individual joints 11 and 12 of the manipulator 4 that are present in the real image, and calculates differences between the identified positions of the individual joints 11 and 12 of the manipulator 4 and the positions of the individual joints 11 and 12 of the manipulator 4 calculated by the image-generating portion 17. The image-processing portion 18 detects and outputs the magnitude of the external force on the basis of the magnitudes of the calculated differences between any of the positions of the joints 11 and 12.

Also, with the medical manipulator system 1 according to this embodiment, in accordance with the magnitude of the external force that is exerted on the manipulator 4 and that is output from the image-processing portion 18, the image-generating portion 17 changes the transparency of the pseudo image of the manipulator 4.

In other words, the image-generating portion 17 sorts the magnitudes of the external forces output from the image-processing portion 18 in multiple steps by using thresholds, and, when the external force is determined to be the lowest, the image-generating portion 17 sets the transparency of the pseudo image at the highest, and changes the transparency of the pseudo image so that the transparency of the pseudo image is decreased with an increase in the magnitude of the external force.

The operation of the thus-configured medical manipulator system 1 according to this embodiment will be described below.

In order to treat an affected portion X inside the body of a patient by using the medical manipulator system 1 according to this embodiment, the endoscope 2 and the manipulator 4 are inserted via the lumens 8 and 9 of the overtube 7, the distal end of which is inserted into the body, and the endoscope 2 and the manipulator 4 are exposed from the distal end of the overtube 7.

When the affected portion X is disposed in the viewing field of the endoscope 2, the real image acquired by the endoscope 2 is displayed on the display portion 6. Because the distal end of the manipulator 4 is displayed on the display portion 6 as a result of the manipulator 4 being inserted and the distal end thereof being disposed in the viewing field of the endoscope 2, the operator can treat the affected portion X by operating the manipulator 4 by manipulating the operating portion 15 while viewing the display portion 6.

When the operating portion 15 is manipulated and manipulating inputs are input, the control signals are generated by the control-signal generating portion 16, the movable portion 13 of the manipulator 4 is operated by operating the driving portion 14, and the pseudo image of the manipulator 4 is generated by the image-generating portion 17 on the basis of the control signals.

Figure 4:
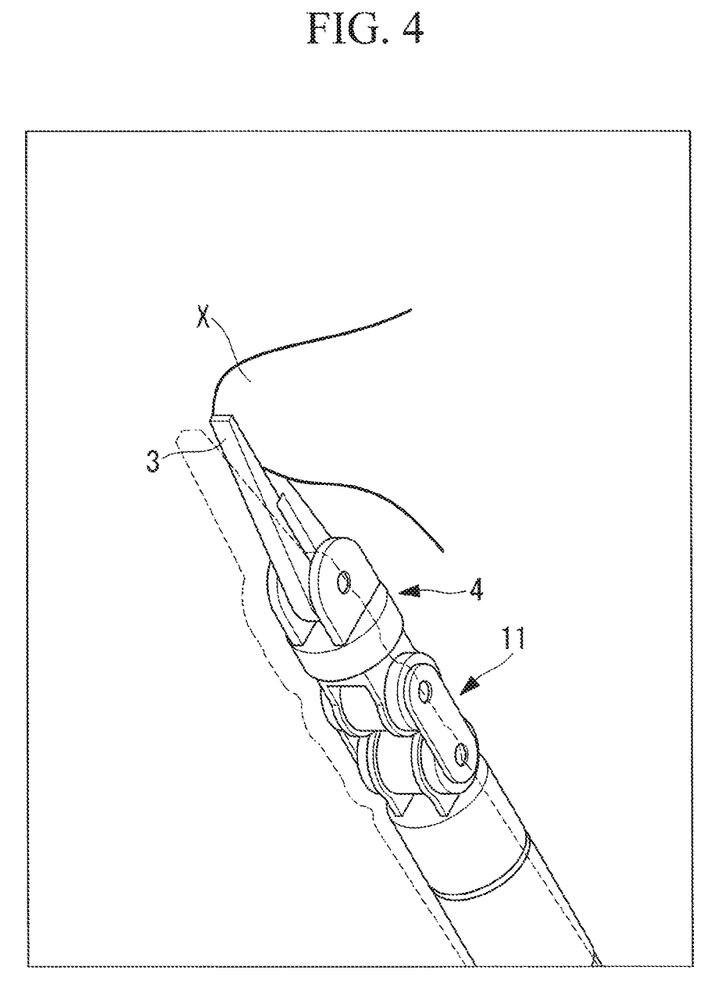
FIG. 4 is a diagram showing an example image to be displayed on a display portion of the medical manipulator system in FIG. 1 in the case in which an external force is low.

In this case, in the state in which the treating portion 3 at the distal end of the manipulator 4 is not in contact with the affected portion X or in the case in which the individual portions of the manipulator 4 are not in contact with tissue, etc. inside the body, a large external force does not act on the manipulator 4, and, as shown in FIG. 4, the manipulator 4 in the real image and the pseudo image of the manipulator 4 generated on the basis of the control signals are displayed at nearly the same positions.

Because of this, the difference, calculated by the image-processing portion 18, between the position of the manipulator 4 in the real image and the position of the pseudo image of the manipulator 4 is close to zero. Therefore, the image-generating portion 17 determines that the external force exerted on the manipulator 4 is low, sets the transparency of the generated pseudo image to be high, and generates a composited imaged in which the pseudo image is superimposed on the real image in such a manner that the pseudo image is displayed inconspicuously.

As a result, because the real image is not blocked by the pseudo image displayed at the position at which the pseudo image is completely overlapping the manipulator 4 in the real image, the pseudo image does not hinder the treatment.

Figure 5:
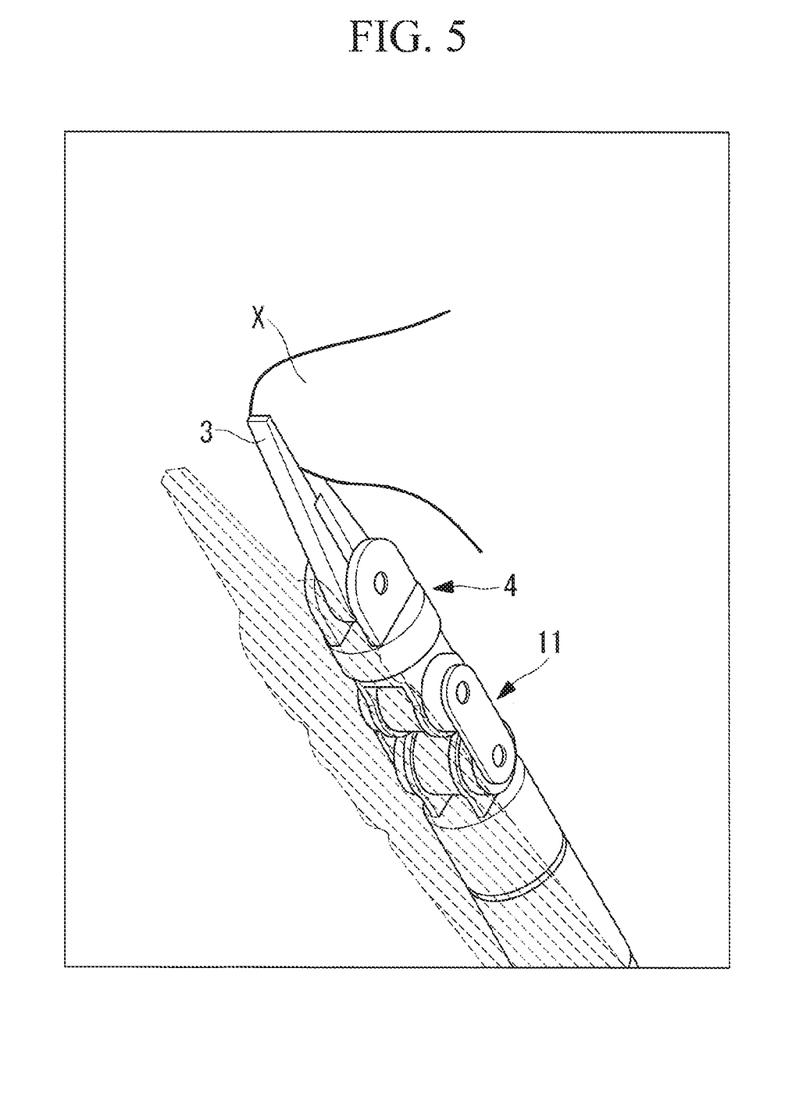
FIG. 5 is a diagram showing an example image to be displayed on the display portion of the medical manipulator system in FIG. 1 in the case in which the external force is intermediate.
Figure 6:
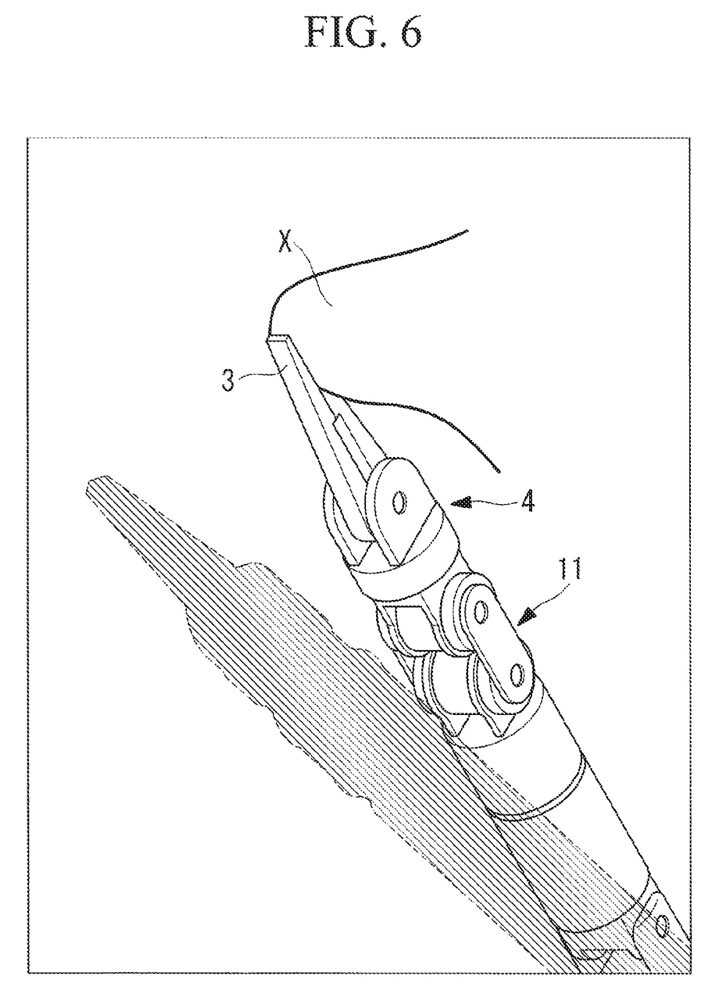
FIG. 6 is a diagram showing an example image to be displayed on the display portion of the medical manipulator system in FIG. 1 in the case in which the external force is high.

On the other hand, when the manipulator 4 is operated in the state in which the treating portion 3 at the distal end of the manipulator 4 is in contact with the affected portion X while performing treatment, the external force that the manipulator 4 receives from the affected portion X increases. Because of this, the difference, calculated by the image-processing portion 18, between the position of the manipulator 4 in the real image and the position of the pseudo image of the manipulator 4 increases, as shown in FIGS. 5 and 6.

Therefore, the image-generating portion 17 determines that the external force exerted on the manipulator 4 is high, sets the transparency of the generated pseudo image to be low, and generates the composited image in which the pseudo image is superimposed on the real image in such a manner that the pseudo image is displayed conspicuously. As a result, the pseudo image, having a low transparency, is displayed at a position displaced from the manipulator 4 in the real image, and it is possible to allow the operator to recognize the fact that the external force exerted on the manipulator 4 has increased.

In this way, with the medical manipulator system 1 according to this embodiment, there is an advantage in that it is possible to notify the operator, in an emphasized manner, about an increase in the external force by changing the display form of the pseudo image, thereby making the pseudo image more conspicuous with an increase in the external force, without blocking the real image when the external force exerted on the manipulator 4 is low.

Note that, in this embodiment, although the transparency of the pseudo image is changed in multiple steps by using the plurality of thresholds, alternatively, the transparency may be changed in a continuous manner in accordance with the difference between the position of the manipulator 4 in the real image and that of the pseudo image of the manipulator 4.

In addition, instead of changing the transparency of the pseudo image or in conjunction therewith, the color of the pseudo image may be changed. In the case in which the external force exerted on the manipulator 4 is high, the manipulator 4 in the pseudo image may be changed to a conspicuous color, and, in the case in which the external force is low, the color thereof may be changed to an inconspicuous color.

For example, regarding a conspicuous color with respect to biological tissue inside the body, which is predominantly red, it is possible to make the pseudo image conspicuous by increasing the intensity of green, which is the complementary color of red.

In addition, in the case in which a line drawing representing the outline of the manipulator 4 or the frame of the manipulator 4 is used as the pseudo image, the transparency of the lines or the color of the lines may be changed in accordance with the magnitude of the external force exerted on the manipulator 4, or the thickness of the lines may be increased with an increase in the magnitude of the external force.

In addition, although the pseudo image of the portion of the manipulator 4 to be displayed on the display portion 6 is generated and the display form of this pseudo image as a whole is changed, alternatively, the display form may be changed for each of the joints 11 and 12 by determining the magnitudes of the external forces for each of the joints 11 and 12.

In addition, an arrow pointing in the direction in which the external force is exerted may be displayed, and the length and/or the thickness of the arrow may be changed in accordance with the magnitude of the external force.

In addition, in this embodiment, the image-processing portion 18 identifies the position of the manipulator 4 in the real image by applying image processing to the real image, and detects the magnitude of the external force exerted on the manipulator 4 by calculating the difference between the identified position and the position of the pseudo image of the manipulator 4 generated by the image-generating portion 17; alternatively, however, the magnitude of the external force may be detected by using other arbitrary methods. For example, because the tensile force in the wire driving the movable portion 13 increases when the external force exerted on the manipulator 4 increases, the magnitude of the external force may be estimated from the magnitude of the tensile force.

In addition, in the case in which it is possible to dispose sensors such as angle sensors, strain gauges, or the like at the individual joints 11 and 12 of the manipulator 4, the external force exerted on the manipulator 4 may be detected on the basis of the outputs from the sensors.

Next, a medical manipulator system 20 according to a second embodiment of the present invention will be described with reference to FIG. 7.

Figure 7:
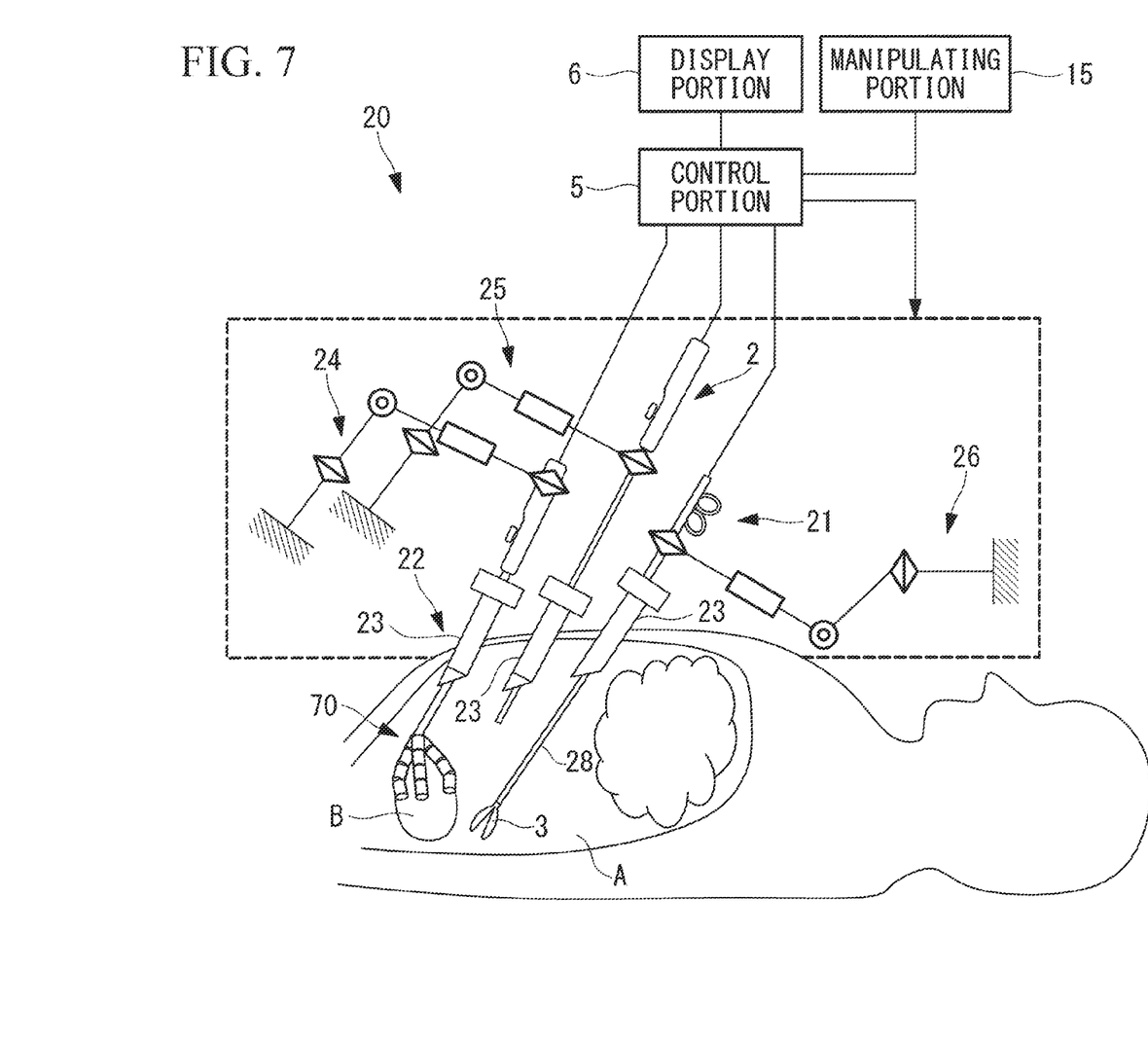
FIG. 7 is an overall configuration diagram showing a medical manipulator system according to a second embodiment of the present invention.

As shown in FIG. 7, the medical manipulator system 20 according to this embodiment differs from the medical manipulator system 1 of the first embodiment in that a rigid manipulator 21 is employed therein. Therefore, in this embodiment, the configuration of the medical manipulator system 20 will mainly be described, and the configurations that are the same as those of the first embodiment will be given the same reference signs and descriptions thereof will be omitted.

As shown in FIG. 7, the medical manipulator system 20 is provided with: the endoscope 2; a manipulator 21; an exclusion instrument 22 that excludes an organ B in an abdominal cavity (body cavity) A; trocars 23 into which the exclusion instrument 22, the endoscope 2, and the manipulator 21 are inserted; multijoint motorized arms 24, 25, and 26 that individually hold proximal-end portions of the exclusion instrument 22, the endoscope 2, and the manipulator 21 outside the body; the operating portion 15 that is manipulated by the operator; the control portion 5; and the display portion 6.

The manipulator 21 is provided with: an elongated inserted portion 28 that can be inserted into the abdominal cavity A; the movable portion 13; and the driving portion 14.

The control-signal generating portion 16 of the control portion 5 generates the control signals for operating the joints of the motorized arms 24, 25, and 26 on the basis of the manipulation inputs that are input via the operating portion 15.

When the operator inputs manipulating inputs via the operating portion 15, signals corresponding to those manipulating inputs are transmitted to the control-signal generating portion 16 of the control portion 5, the control-signal generating portion 16 generates the control signals for operating the joints on the basis of the received signals, and the motorized arms 24, 25, and 26 are operated on the basis of the generated control signals. By doing so, the operator can remotely operate, via the operating portion 15, the exclusion instrument 22, the endoscope 2, and the manipulator 21 that are inserted into the body cavity.

Furthermore, the control-signal generating portion 16 receives detected values from encoders (not shown) that are provided in the motorized arms 24, 25, and 26 and that detect rotational angles of the individual joints, and calculates the positions and orientations of the exclusion instrument 22, the endoscope 2, and the manipulator 21 on the basis of the received detected values from the encoders. Also, the control-signal generating portion 16 generates control signals for operating the joints of the motorized arm 24 holding the exclusion instrument 22 so as to move the exclusion instrument 22 on the basis of the calculated positions and orientations of the endoscope 2 and the manipulator 21. Specifically, when the endoscope 2 and the manipulator 21 approach the exclusion instrument 22, and the distances to the exclusion instrument 22 therefrom fall below a predetermined threshold, the control-signal generating portion 16 generates the control signals for operating the joints of the motorized arm 24 so that the exclusion instrument 22 is moved in a direction away from the endoscope 2 or the manipulator 21.

With the thus-configured medical manipulator system 20, when the manipulator 21 approaches the exclusion instrument 22 while treatment is being performed by operating the endoscope 2 and the manipulator 21 in the abdominal cavity A, the exclusion instrument 22 is automatically moved so as to be moved away from the manipulator 21 which causes the organ B positioned in the vicinity of the manipulator 21 to be further excluded, and thus, a treatment space for the manipulator 21 is newly ensured. Similarly, when the endoscope 2 approaches the exclusion instrument 22, the exclusion instrument 22 is automatically moved so as to be moved away from the endoscope 2, thus ensuring a viewing field for the endoscope 2. As has been described above, by moving the exclusion instrument 22 in association with the operation of other medical equipment that is simultaneously used with the exclusion instrument 22, there is an advantage in that it is possible to further increase the efficiency of surgery.

In this case, with the medical manipulator system according to this embodiment, the image-generating portion 17 generates pseudo images of the manipulator 21 and the exclusion instrument 22 on the basis of the control signals. Also, the transparencies of the pseudo images are set on the basis of the differences, calculated by the image-processing portion 18, between the positions of the manipulator 21 and the exclusion instrument 22 in the real image and the positions of the pseudo images of the manipulator 21 and the exclusion instrument 22.

As a result, in the case in which the pseudo images of the manipulator 21 and the exclusion instrument 22 completely overlap with the manipulator 21 and the exclusion instrument 22 in the real image, the transparencies thereof are set to be high, and, because the pseudo images do not block the real image, the pseudo images do not hinder the treatment. On the contrary, when the manipulator 21 and the exclusion instrument 22 are operated in the state in which the distal ends, etc. of the manipulator 21 and the exclusion instrument 22 are in contact with the affected portion X while performing treatment, the external forces that the manipulator 21 and the exclusion instrument 22 receive from the affected portion X increase. Because of this, the differences, calculated by the image-processing portion 18, between the positions of the manipulator 21 and the exclusion instrument 22 in the real image 22 and the positions of the pseudo images of the manipulator 21 and the exclusion instrument 22, increase.

In this case, the image-generating portion 17 determines that the external forces exerted on the manipulator 21 and the exclusion instrument 22 are high, sets the transparencies of the generated pseudo images to be low, and generates a composited image in which the pseudo images are superimposed on the real image in a conspicuous display form. As a result, the pseudo images, having low transparencies, are displayed at positions displaced from the positions of the manipulator 21 and the exclusion instrument 22 in the real image, and it is possible to allow the operator to recognize the fact that the external forces exerted on the manipulator 21 and the exclusion instrument 22 have increased.

The above-described embodiment leads also to the following invention.

An aspect of the present invention is a medical manipulator system including: a manipulator that has a treating portion at a distal end thereof; a control portion that controls the manipulator; an endoscope that captures an image showing a state of the treating portion performing treatment by means of the manipulator; an external-force detecting portion that detects an external force exerted on the manipulator; an image-generating portion that generates a pseudo image of the manipulator at a position based on a control signal generated by the control portion, and that generates a composited image in which the pseudo image is superimposed on a real image acquired by the endoscope; and a display portion on which the composited image generated by the image-generating portion is displayed, wherein the image-generating portion changes a display form of the pseudo image on the basis of the magnitude of the external force detected by the external-force detecting portion.

With this aspect, when the manipulator and the endoscope are inserted into the body and are brought close to an affected portion and when an image showing the state of the affected portion being treated by the treating portion of the manipulator is captured by the endoscope, the real image of the endoscope acquired by the endoscope is displayed on the display portion, and the pseudo image of the manipulator generated by the image-generating portion is superimposed on the real image and displayed on the display portion. Because the pseudo image is generated at the position based on the control signal generated by the control portion, in the case in which the external force is exerted on the manipulator and the movement thereof is restricted, displacement occurs between the manipulator in the real image and the pseudo image thereof.

In this case, because the image-generating portion changes the display form of the pseudo image in accordance with the magnitude of the external force detected by the external-force detecting portion, it allows display forms to be different between the case in which the external force is high and the case in which the external force is low. By doing so, in the case in which the external force exerted on the manipulator is high, it is possible to perform a display that allows the fact that the external force exerted on the manipulator is high to be perceived, thus making it possible to call the attention to the operator. In addition, by displaying the pseudo image so as to be inconspicuous in the case in which the external force exerted on the manipulator is low, it is possible to prevent the pseudo image from blocking the real image.

In the above-described aspect, the image-generating portion may change the display form of the pseudo image so as to be more conspicuous in the composited image with an increase in the magnitude of the external force detected by the external-force detecting portion.

By doing so, because the manipulator in the real image and the pseudo image thereof are separated from each other with an increase in the external force exerted on the manipulator, it is possible to call the attention to the operator by making the pseudo image conspicuous. In addition, by displaying the pseudo image so as to be inconspicuous in the case in which the external force exerted on the manipulator is low, it is possible to prevent the pseudo image from interfering with the real image.

In addition, in the above-described aspect, the image-generating portion may decrease the transparency of the pseudo image with an increase in the magnitude of the external force detected by the external-force detecting portion.

By doing so, because the transparency of the pseudo image is decreased with an increase in the external force exerted on the manipulator, it is possible to call the attention to the operator by making the pseudo image conspicuous. In addition, by increasing the transparency in the case in which the external force exerted on the manipulator is low, it is possible to display the pseudo image so as to be inconspicuous, and thus, it is possible to prevent the pseudo image from interfering with the real image.

In addition, in the above-described aspect, the image-generating portion may change a color of the pseudo image to a more conspicuous color with an increase in the magnitude of the external force detected by the external-force detecting portion.

By doing so, because the color of the pseudo image is changed to the conspicuous color with an increase in the external force exerted on the manipulator, it is possible to call the attention to the operator by making the pseudo image conspicuous. In addition, the pseudo image may be displayed in the inconspicuous color in the case in which the external force exerted on the manipulator is low, and thus, it is possible to prevent the pseudo image from interfering with the real image.

In addition, in the above-described aspect, the image-generating portion may generate the pseudo image in the form of a line drawing and changes lines in the pseudo image so that the thickness thereof is increased with an increase in the magnitude of the external force detected by the external-force detecting portion.

By doing so, because the thickness of the lines in the pseudo image formed of the line drawing is increased with an increase in the external force exerted on the manipulator, it is possible to call the attention to the operator by making the pseudo image conspicuous. In addition, by decreasing the thickness of the lines in the pseudo image in the case in which the external force exerted on the manipulator is low, it is possible to prevent the pseudo image from interfering with the real image.

In addition, in the above-described aspect, the external-force detecting portion may detect a position of the manipulator by processing the real image, and may detect the external force on the basis of a difference between the detected position and the position of the pseudo image of the manipulator generated by the image-generating portion.

By doing so, the real image acquired by the endoscope is processed by the external-force detecting portion and the position of the manipulator is detected; the difference between the detected position and the position of the pseudo image of the manipulator generated by the image-generating portion is calculated; and the magnitude of the external force is detected in accordance with the magnitude of the difference. By doing so, it is possible to detect, without providing a special sensor, the magnitude of the external force exerted on the manipulator by processing the endoscope image.

In addition, in the above-described aspect, the manipulator may be driven by means of a wire, and the external-force detecting portion may detect the external force on the basis of a tensile force in the wire.

By doing so, because the tensile force in the wire that drives the manipulator increases when the external force is exerted on the manipulator, it is possible to detect the external force by detecting the tensile force.

REFERENCE SIGNS LIST 1, 20 medical manipulator system
2 endoscope
3 treating portion
4, 21 manipulator
22 exclusion instrument (manipulator)
6 display portion
16 control-signal generating portion (control portion)
17 image-generating portion
18 image-processing portion (external-force detecting means)

The invention claimed is:

1. A medical manipulator system comprising:
a manipulator comprising a treating portion at a distal end thereof;
an endoscope configured to capture an image showing a state of the treating portion; and
a controller comprising at least one processor, wherein the at least one processor is configured to:
receive the image from the endoscope;
determine a magnitude of an external force exerted on the manipulator based on the state of the treating portion of the manipulator shown in the image;
generate an auxiliary image in which a display form thereof is changed so that transparency of the auxiliary image is decreased with an increase in the magnitude of the external force exerted on the manipulator determined;
determine a display position of the auxiliary image in the image on the basis of the magnitude of the external force exerted on the manipulator determined;
generate a composited image signal of a composited image in which the auxiliary image is superimposed on the image on the basis of the display position determined; and
control a display to display the composited image based on the composited image signal.

2. The medical manipulator system according to claim 1, wherein the auxiliary image is a pseudo image of the manipulator.

3. A medical manipulator system comprising:
a manipulator comprising a treating portion at a distal end thereof;
an endoscope configured to capture an image showing a state of the treating portion; and
a controller comprising at least one processor, wherein the at least one processor is configured to:
receive the image from the endoscope;
determine a magnitude of an external force exerted on the manipulator based on the state of the treating portion of the manipulator shown in the image;
generate an auxiliary image of the manipulator in which a display form thereof is changed so that a color of the auxiliary image is changed with an increase in the magnitude of the external force exerted on the manipulator determined;
determine a display position of the auxiliary image in the image on the basis of the magnitude of the external force exerted on the manipulator determined;
generate a composited image signal of a composited image in which the auxiliary image is superimposed on the image on the basis of the display position determined; and
control a display to display the composited image based on the composited image signal.

4. A medical manipulator system comprising:
a manipulator comprising a treating portion at a distal end thereof;
an endoscope configured to capture an image showing a state of the treating portion; and
a controller comprising at least one processor, wherein the at least one processor is configured to:
receive the image from the endoscope;
determine a magnitude of an external force exerted on the manipulator based on the state of the treating portion of the manipulator shown in the image;
generate an auxiliary image in which a display form thereof is changed so that thickness of lines of the auxiliary image is thicker with an increase in the magnitude of the external force exerted on the manipulator determined;
determine a display position of the auxiliary image in the image on the basis of the magnitude of the external force exerted on the manipulator determined;

generate a composited image signal of a composited image in which the auxiliary image is superimposed on the image on the basis of the display position determined; and control a display to display the composited image based on the composited image signal.

5. A method of controlling a medical manipulator system including a manipulator including a treating portion at a distal end thereof, and an endoscope configured to capture an image showing a state of the treating portion, the method comprising:

receiving the image from the endoscope;

determining a magnitude of an external force exerted on the manipulator based on the state of the treating portion of the manipulator shown in the image;

generating an auxiliary image in which a display form thereof is changed so that transparency of the auxiliary image is decreased with an increase in the magnitude of the external force exerted on the manipulator determined;

determining a display position of the auxiliary image in the image on the basis of the magnitude of the external force exerted on the manipulator determined;

generating a composited image signal of a composited image in which the auxiliary image is superimposed on the image on the basis of the display position determined; and controlling a display to display the composited image based on the composited image signal.

6. The method according to claim 5, wherein the auxiliary image is a pseudo image of the manipulator.

7. A method of controlling a medical manipulator system including a manipulator including a treating portion at a distal end thereof, and an endoscope configured to capture an image showing a state of the treating portion, the method comprising:

receiving the image from the endoscope;

determining a magnitude of an external force exerted on the manipulator based on the state of the treating portion of the manipulator shown in the image;

generating an auxiliary image of the manipulator in which a display form thereof is changed so that a color of the auxiliary image is changed with an increase in the magnitude of the external force exerted on the manipulator determined;

determining a display position of the auxiliary image in the image on the basis of the magnitude of the external force exerted on the manipulator determined;

generating a composited image signal of a composited image in which the auxiliary image is superimposed on the image on the basis of the display position determined; and controlling a display to display the composited image based on the composited image signal.

8. A method of controlling a medical manipulator system including a manipulator including a treating portion at a distal end thereof, and an endoscope configured to capture an image showing a state of the treating portion, the method comprising:

receiving the image from the endoscope;

determining a magnitude of an external force exerted on the manipulator based on the state of the treating portion of the manipulator shown in the image;

generating an auxiliary image in which a display form thereof is changed so that thickness of lines of the auxiliary image is thicker with an increase in the magnitude of the external force exerted on the manipulator determined;

determining a display position of the auxiliary image in the image on the basis of the magnitude of the external force exerted on the manipulator determined;

generating a composited image signal of a composited image in which the auxiliary image is superimposed on the image on the basis of the display position determined; and controlling a display to display the composited image based on the composited image signal.

* * * * *